United States Patent

Thomas

(10) Patent No.: US 6,824,125 B2
(45) Date of Patent: Nov. 30, 2004

(54) SIMPLE METHOD FOR THE CONTROLLED PRODUCTION OF VORTEX RING BUBBLES OF A GAS IN A LIQUID

(76) Inventor: Andrew S. W. Thomas, 1703 Barleton Way, Houston, TX (US) 77058

( * ) Notice: Subject to any disclaimer, the term of this patent is extended or adjusted under 35 U.S.C. 154(b) by 77 days.

(21) Appl. No.: 10/237,437

(22) Filed: Sep. 10, 2002

(65) Prior Publication Data

US 2004/0051187 A1 Mar. 18, 2004

(51) Int. Cl.$^7$ .................................................. B01F 3/04
(52) U.S. Cl. ...................... 261/64.3; 261/65; 261/121.1; 261/124
(58) Field of Search ........................ 261/62, 64.1, 64.3, 261/65, 121.1, 124, DIG. 74

(56) References Cited

U.S. PATENT DOCUMENTS

| | | | | |
|---|---|---|---|---|
| 3,589,603 A | * | 6/1971 | Fohl | 239/11 |
| 4,534,914 A | * | 8/1985 | Takahashi et al. | 261/64.3 |
| 5,100,242 A | * | 3/1992 | Latto | 366/267 |
| 5,159,956 A | * | 11/1992 | Kurihara | 137/624.13 |
| 5,218,986 A | * | 6/1993 | Farwell | 137/14 |
| 5,947,784 A | * | 9/1999 | Cullen | 446/15 |
| 6,488,270 B2 | * | 12/2002 | Whiteis | 261/62 |

\* cited by examiner

Primary Examiner—Scott Bushey

(57) ABSTRACT

An apparatus, and its method of operation, are described that allow for the production of gas-filled vortex rings in a host liquid. A source of gas under pressure is connected via a tube to the inlet of a regulation valve whose outflow is connected via a similar tube to an accumulator volume. The accumulator has an outlet that feeds the gas in the accumulator to an electrically operated solenoid valve that is normally closed. The outlet of this valve leads to a nozzle that protrudes upwards into a vessel containing the liquid in which it is desired to form the rings. Upon receiving an electrical pulse of known duration, the solenoid valve opens for that duration and allows a momentary pulse of gas to flow from the accumulator into the nozzle. If the pulse duration is correctly set, a vortex bubble forms at the exit of the nozzle which self-organizes into a defined ring once the gas flow ceases. As the ring advances upwards under the influence of buoyancy force, it pinches off from the gas in the nozzle that remains captive at the nozzle exit under the influence of capillary, or surface tension forces. The device is then ready for the production of another ring upon receipt of another electrical pulse. Different nozzle exit geometries that facilitate this process are described, as well as different configurations of the invention and different applications or implementations of the invention. The invention is unique in that it allows easy, direct and independent control of the parameters that determine ring formation. It can operate under a broad range of these parameters to produce a broad range of sizes of rings, from small to large, and from thick to thin, either in isolation, or in multiples, or in sequential arrays.

4 Claims, 5 Drawing Sheets

SIMPLE METHOD FOR THE CONTROLLED PRODUCTION OF VORTEX RING BUBBLES OF A GAS IN A LIQUID

BACKGROUND OF THE INVENTION

1. Technical Field

The invention relates to an apparatus and method for producing vortex ring bubbles of a gas in a host liquid. It allows these rings to be continually generated under conditions in which the parameters of their generation can be independently controlled over a wide range. It therefore allows one device to produce, within limits, a range of different rings from slow-moving, large rings, to fast-moving, small rings and various combinations in between.

2. Description of the Prior Art

Some forty years ago it was first reported that it that it is possible to generate toroidal ring-shaped bubbles, or ring bubbles as they were then called, of gas rising in liquids. These are in fact vortex rings in which the gas collects in the ring-shaped core and which is thereby made visible as a circular tube of gas. In recent years it has become appreciated that they are a natural phenomenon and have even been observed to be produced by whales and dolphins evidently simply for amusement. Apparently they do this by rapidly exhaling a short pulse of air which self organizes into the ring. Skilled professional divers have also been known to produce them by carefully exhaling a pulse of air upwards. It is now known that the key to formation of ring bubbles lies in the momentary flow of a gas, i.e. a pulse of gas, through a nozzle into a surrounding liquid medium. This is the natural phenomenon that whales and dolphins have learned to exploit, but not just any pulse of gas will work. Apparently, proper adjustment of the parameters that determine the pulse characteristics is critical if rings are to form, as opposed to just normal chaotic plumes of bubbles. It is well known that for a given nozzle shape, there are two parameters that determine the behavior of this kind of pulsed nozzle flow. One is the pressure of the source that establishes the strength of the pulse. Good flow will arise if this pressure is constant and does not decay while the flow exits the nozzle. The other parameter is the time duration of that pulse. Evidently, if both these parameters are within certain ranges of values rings will form, but outside of those ranges rings will not form. Instead, single bubbles or chaotic turbulent jets of bubbles will be obtained. Additionally, variations of these parameters, within the ranges, can be expected to give rise to different kinds of rings. For example, low source pressures, and long duration pulses will generally give rise to large slow moving rings. Conversely, higher pressures and shorter pulses will give rise to smaller, faster moving rings. Ideally, any apparatus designed to generate these rings should allow the operator to easily change the values and thereby create rings of different shape and velocity.

It has often been argued that these toroidal bubbles are analogous to the familiar smoke rings in air. However, they are much more complex as two distinct fluid phases are involved, namely the liquid medium, and the tubular core of gas. It has been known for over a hundred years that a tube of gas in a liquid should spontaneously collapse and break up through the effect of surface tension instability. That this does not happen for the toroidal tube of the ring bubble can be attributed to the stabilizing influence of the circulation around the tubular core. The centrifugal force of the liquid spinning around the core opposes and balances the collapsing force of the surface tension. For the vortex ring bubble, there is also an upward buoyancy force present but that is balanced by a downward cross-flow force arising from the lateral spread of the spinning core of the ring, analogous to the lateral force on a spinning ball. Thus the ring, once formed, will steadily rise and spread out and thin. However, eventually a point is reached where viscosity dampens the energy of the circulation so that surface tension then dominates leading to breakup of the ring. Despite this, very long lived rings can be created before breakup occurs.

Various U.S. patents document methods of producing vortex rings of different co-mingled fluids. U.S. Pat. No. 3,589,603 by Fohl allows two different fluids to come together in a co-annular nozzle and mix to form a vortex ring. The fluid motions are generated by two moving pistons, but the device does not consider the case of one fluid being a liquid and the other being a gas as would be needed for forming a gas-filled ring bubble. The inventor gives no evidence that the device could produce toroidal ring bubbles. U.S. Pat. No. 5,100,242 by Latto uses a technique in which a moving orifice plate generates a ring vortex that can be used to enhance fluid mixing. The inventor claims it can be used in water to produce aerated rings through seeding of the vortex flow with bubbles, but this is not the same as producing ring bubbles which are single, coherent self-organized structures. These structures require very specialized conditions of pulse flow and pulse duration. One example, U.S. Pat. No. 4,534,914 to Takahashi et al. does provide those conditions and describes a device that uses an accumulator with a diaphragm in one wall that unseats a spring loaded valve when under pressure allowing gas to flow out into a nozzle. The nozzle has a second elastic valve at its exit which is driven open by the pressure it is exposed to following the opening of the spring valve. As the flow exits through the two valves, the pressure in the accumulator falls, both valves close, leaving a gas-filled ring vortex forming at the tip of the second elastic valve. In a second embodiment, they replace the spring-loaded valve with an electrically-driven valve and a pressure sensitive switch on the diaphragm inside the accumulator. This electrically-driven valve allows the gas in the accumulator to flow to, and open the second elastic valve once a predefined pressure is reached. After the flow starts and the pressure in the accumulator begins to fall, the diaphragm moves against the switch to close the electric valve. In a third embodiment, they use a timed pulse to an electrically-actuated valve, but the valve is now placed externally upstream of the accumulator so as to feed gas to the accumulator. Opening the electric valve causes the pressure to start to rise in the accumulator, eventually forcing the second elastic valve open, thereby creating the flow. This flow through the second elastic valve continues even after the electric valve is closed and does not stop until the pressure in the accumulator falls below a certain level so that the second elastic valve will close.

An examination of the devices of Takahashi et al. points out the following operating characteristics:

1. The pressure levels where the valves open and close can not be externally controlled, since these are a consequence of the resilience of the valves and of the valve springs in the first embodiment, or of the diaphragm in the second and third embodiments, as well as the resiliency of the second exit valve.
2. In the first embodiment, a pulsed flow is established, but the duration of the flow is not determined by any external timing pulse, but by the pressure-induced movement of the diaphragm against the resiliency of the spring of the first valve. Likewise, the second embodiment uses an electrically operated valve, but nor is it driven by any external timing pulse. It is also activated and deactivated by the pressure-induced deflection of the diaphragm contacting a mechanical switch. Therefore in both embodiments, the duration of the pulse can not be easily changed without changing the mechanical elements of the device.

3. The third embodiment also uses an electrically operated valve, but the timing of that valve does not directly define the time duration of the pulse flow. Opening the electrically-driven valve merely starts to pressurize the accumulator, and it is that pressure that ultimately unseats the second elastic valve, starting the flow. Further, once started, the electric valve does not, and can not shut off the flow through the second elastic valve since it only controls the flow into the accumulator. Instead, it is the volume of the accumulator, the resiliency of the elastic valve and the source pressure that determine when that valve will close. These can not be easily independently controlled or varied in a single device. Therefore, significant reconfiguration of the apparatus is needed to change the parameters as needed for generating vortex rings of different sizes and circulation.

4. All these embodiments use a second valve at the nozzle exit and this is essential for proper operation of the devices. Indeed, the devices will not operate without that additional second valve.

5. In all three cases, the pressure in the accumulator is not constant but must decay during operation if the devices are to work. Whether or not this kind of pressure profile is essential, or even optimal for the formation of gas-filled rings is not clear.

6. With each of the three embodiments, the operator can not be precisely certain as to the exact time when the ring will start to form once the accumulator is raised in pressure as it depends on how quickly gas is fed into the accumulator and when it unseats the valve.

In another example, in U.S. Pat. No. 5,947,784 to Cullen, a very similar device is described. In one embodiment it uses a small spring loaded annular nozzle at the end of a tube into which an operator blows to unseat the valve momentarily and create the ring. That inventor recommends that an annular nozzle is to be preferred since an annular ring is to be generated. The skill of the operator, who effectively acts as another second valve, is what determines the strength and duration of the pulse that creates the vortex ring.

In a second embodiment, the pulse is created by an electrically driven pump actuated by a timed circuit. This is very similar to the third embodiment of Takahashi et al. As before, the pressure at which the vortex forms is a consequence of the resilience of the valves, and the duration of the pulse is also determined by this pressure and the volume of the tubing feeding the valve. Only by using a host of different valves and different sizes of tubing can different pressures and pulse durations be achieved. Changes to these parameters can not be easily implemented without reconfiguration of the apparatus.

The method described by Whiteis (U.S. Pat. No. 6,488,270) is somewhat different and allows a flowing gas to build up in a contained pocket under a plate that tilts around a pivot in response to the gas buildup. This flows the gas to a nozzle and allows it to momentarily escape into the surrounding liquid. In this device, the gas flows out of the nozzle because it is at a higher pressure than the pressure at the exit port on the top of the plate. This is because there is a hydrostatic pressure difference between the contained gas beneath the plate and the nozzle exit. This pressure is not constant during operation, but changes as the gas flows out of the nozzle. The duration of the flow through the nozzle is determined by this varying pressure as well as by the geometry of the tilt mechanism and the size of the captured gas pocket. In a second variation, the gas is fed to an inverted bell-like container and is released by an operator momentarily depressing a lever that opens a valve at the top of the bell thereby creating a flow out of the container. The duration of the flow is determined by the skill of the operator and can not be independently established. In both embodiments, different apparatus will be needed for generating vortex rings of different properties. In particular, both these apparatus, as well as the other devices that have been described, do not lend themselves to producing intense, fast spinning vortex rings, since their mechanical moving parts will not allow either very high pressures or very fast, short duration pulses to be easily established.

Of the various inventions described, only those of Takahashi et al. (U.S. Pat. No. 4,534,914), Cullen (U.S. Pat. No. 5,947,784) and Whiteis (U.S. Pat. No. 6,488,270) do enable the unique conditions of flow to be established such that gas-filled, ring bubbles can form. They all make use of specially configured valves, or the creation of a momentary gas flow, in an attempt to establish the favorable conditions of pressure and pulse duration that are necessary to give rise to gas-filled vortex rings. However, from the preceding discussion, a number of limitations or shortcomings can be identified and which can be summarized as:

1. The various configurations generally require the valve to be at the nozzle exit, or even require the complication of an additional second valve right at the nozzle exit.
2. None of these devices allows easy, independent and direct control of the source pressure. Significant changes to the configuration of the devices are needed to change the operating pressure. Also, some of these inventions even require a falling pressure so as to operate. Actually, it is not clear what is the best or simplest pressure variation during the pulse that will ensure producing ring bubbles as opposed to trails of random bubbles. Indeed, without experimentation, it is by no means obvious that other concepts will even be able to produce the right pressure conditions that favor the formation of organized bubble rings.
3. None of these devices allows easy, independent and direct control of the pulse duration. In the configurations that have been described, this can also only be changed by making significant changes to the configuration of the devices. They do not allow the conditions of operation to be easily "dialed in" by the operator.
4. The available range of operation for the devices is limited and they essentially operate at only one condition of pressure and pulse duration for a given geometry. In that sense they can be thought of as "point designs" with limited operational range. For example, the devices do not lend themselves easily to the generation of small rings which require very short pulse durations and higher source pressures.
5. Further, none of the devices allow the precise time of initiation of the pulse to be defined, but only the start of a sequence of events that may ultimately lead to a pulse and subsequent ring formation. This can be important if there is a desire to have the ring form at a very specific time, as might be the case in scientific applications, or if there is a desire to photograph or film the evolution of the ring, or if it desired to produce controlled sequences of these rings, all of which might require timing the pulse to within a small fraction of a second.

BRIEF SUMMARY OF THE INVENTION

It is therefore the object of the invention to provide a simple and direct means of creating the right conditions of pressure and pulse duration of source flow that will give rise to ring bubbles of a gas in a liquid medium while minimizing the number of mechanical valves etc.

It is another object of the invention to provide a means for generating these rings under conditions in which the pressure of the source flow may be directly, precisely, independently and repeatedly controlled with ease.

It is another object of the invention to provide a means for generating these rings under conditions in which the duration of the pulse of the source flow may be directly, precisely, independently and repeatedly controlled with ease.

It is yet another object of the invention that these rings can be created under a wide range of conditions, so that thin rings of fast rotation and fast translation or thick rings of slow rotation and slow translation can be established with the same apparatus.

It is yet another object of the invention to allow these rings to be created at precisely predetermined times so that they may be created sequentially with the frequency of generation being independently determined and controlled.

To achieve these objectives, an apparatus is described in which an accumulator volume is pressurized with a regulated supply of gas under pressure. This confined gas is connected via a tube to the inlet of an electrically operated solenoid valve that can be opened or closed with a standard electrical timing circuit. The outgoing flow from this valve is directed through a nozzle that protrudes into a tank of liquid.

In operation, the electronic circuitry creates an electrical pulse that momentarily opens the solenoid valve, allowing the gas to flow momentarily from the accumulator into the nozzle. If the gas pressure is within a certain range, and if the electrical pulse is of an appropriate duration, a gas-filled vortex ring, or ring bubble will form and be buoyantly carried upwards away from the nozzle.

To eliminate the need for extra valves, a novel geometry is presented that best allows this to take place and is one that exploits the surface tension or capillary properties of the host liquid and will depend on the exit area that is desired. Various configurations are described that achieve this and include circular nozzle exits for small nozzles, or flattened nozzle exits or exits covered with fine wire meshes for larger nozzle exits.

Other features and embodiments of the invention will become apparent from the following drawings and descriptions that are provided.

BRIEF DESCRIPTION OF THE DRAWINGS

The objects and features if the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE INVENTION

Technical Background

The following description is provided to enable any person skilled in the art to make and use the invention and sets forth the best modes contemplated by the inventor of carrying out his invention. Various modifications, however, will remain readily apparent to those skilled in the art.

Figure 1:
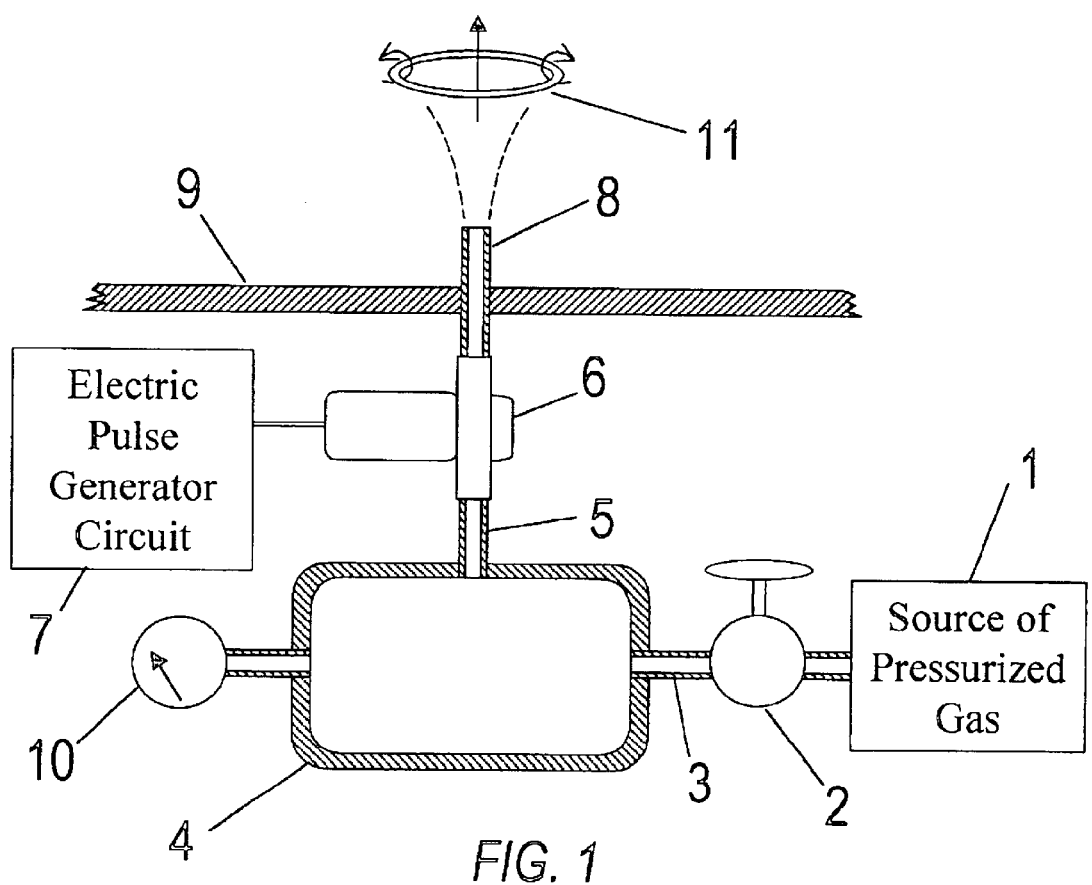
FIG. 1 is a schematic of the preferred and simplest embodiment of the invention. It is suggested that this view be on the front page of the published patent application.

FIG. 1 depicts the simplest embodiment of the invention for producing and controlling the production of gas-filled vortex rings in a liquid medium. The device consists of a source of gas 1 that may be a tank under pressure or a pump, that is connected through a simple regulating valve 2 and through a feed tube 3 to a contained volume 4 that acts as an accumulator. Another tube, 5, exits this accumulator and is connected to the inlet of an electrically operated solenoid valve, 6 that is normally closed. These kinds valves are readily available commercially and make use of an electric solenoid to open and close a diaphragm or to pinch off a resilient tube. This valve is actuated by a standard electric circuit, 7, that generates a short electrical pulse that opens the solenoid valve 6. Such circuitry is also widely known and can generate electrical pulses of precisely known duration that can be easily varied by simply adjusting an electrical potentiometer or resistor. At the exit of the valve is a tube 8 that passes upwards through the floor 9 of a tank containing the host liquid. This tube protrudes slightly above the floor of the tank and its open end acts as the nozzle at which the ring bubble, 11, is to be formed. In the simplest configuration of the invention, the open end of this tube is circular, but need not be.

Figures 2A, 2B, 2C, 2D:
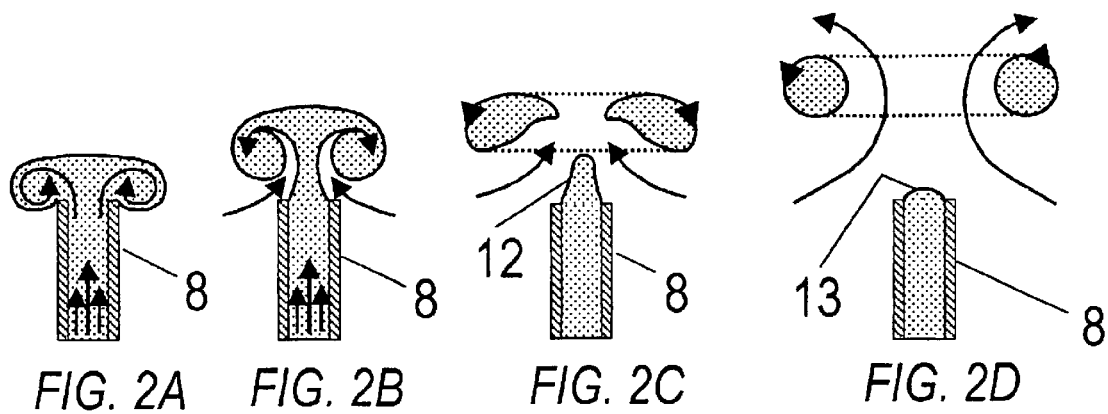
FIG. 2A, FIG. 2B, FIG. 2C and FIG. 2D depict in cross-section, the sequence of events that takes place during operation of the invention and which gives rise to the gas-filled ring bubble.

In its operation, the gas is allowed to pressurize the accumulator to any desired level. This level may be directly measured by a pressure transducer or gauge, 10, and can be set at any desired level by means of the regulating valve 2. An electrical pulse of the desired duration is generated by the circuit 7 and is used to momentarily open the valve 6. This creates an impulsively started flow of the gas from the accumulator 4, through the tubing 5 and valve 6 and exiting the nozzle 8. A bubble forms at the exit of this tube as the gas flows into the liquid medium and it is this bubble that becomes the ring after the valve closes and the flow ceases. This process of ring formation is depicted in the sequences of cross sections shown in FIGS. 2A, 2B, 2C and 2D. In the proper language of the science of fluid mechanics, as the gas is impulsively accelerated through the nozzle 8, vorticity is generated by viscous friction within the tube and this vorticity feeds a developing or starting vortex with its attendant circulation at the nozzle exit as in FIG. 2A. A combination of the upward momentum of the emerging gas stream and the induced flow from the circulation of the starting vortex will then draw the surrounding liquid up into and through the center of the emerging bubble as depicted in FIG. 2B. If the timing is correct, the valve now closes and the gas flow from the accumulator ceases. Capillary or surface tension forces then cause the rising vortex bubble to pinch off from the gas in the nozzle as in FIG. 2C. The vortex bubble then self organizes and stabilizes under the influence of capillary or surface tension forces into a rising ring shown in cross section in FIG. 2D. Because the parameters of pressure and pulse duration can be directly and repeatedly controlled to any desired values with this invention, then the geometry of these rings can be directly controlled.

An important feature of this embodiment is that a second valve is not needed at the exit of the nozzle 8. This is because the invention exploits the natural surface tension properties of the gas-liquid interface so that when the valve closes and the gas flow ceases, the column of gas 12 breaks off from the developing ring as shown in FIG. 2C. Importantly, the column of gas 12 that is left protruding from the nozzle is held in place by the capillary or surface tension forces of the curved gas/liquid surface at the exit plane of the nozzle. Those forces pull it into the curved shape 13 where it remains pinned and stabilized at the exit of the nozzle leaving a static column of gas held in the nozzle tube. The device is now ready for the cycle to be repeated through another commanded opening of the valve, causing that column of gas to be impulsively started, so that another ring may be quickly generated independent of the first, but with the same properties. This pinning of the gas column in the nozzle is important since any liquid that flows back and gets trapped in the tube 8, will spurt out at the start of the next valve opening and interfere with the sequence depicted in FIGS. 2A, 2B, 2C and 2D. Other inventors (such as Takahashi et al., U.S. Pat. No. 4,534,914) place a second valve at the nozzle exit to prevent this. In this invention, novel use is made of the surface tension forces so that liquid will not back flow into the nozzle, provided it is not too large in diameter. Therefore an additional valve at the exit plane of the nozzle is not needed.

Figures 3A, 3B, 3C, 4A, 4B:
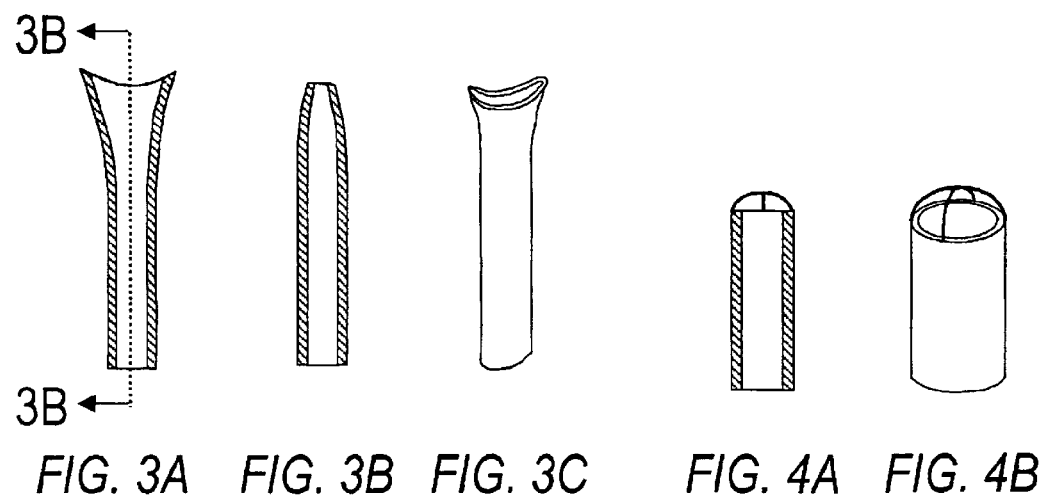
FIG. 3A, FIG. 3B and FIG. 3C depict a different design of a larger discharge nozzle that will enhance surface tension forces to produce vortex ring bubbles when using the invention with larger nozzles.
FIG. 4A, and FIG. 4B depict yet another different design of a larger discharge nozzle that will enhance surface tension forces to produce vortex ring bubbles when using the invention with still larger nozzles.

Larger nozzles can be accommodated thorough another important feature claimed in this invention, namely that the nozzle exit need not be circular. Indeed, for larger diameter nozzles, the capillary forces that restrain the column of air 13 become too small, since it is well known that capillary force varies as the inverse of the radius of curvature of the surface separating the gas at the nozzle exit and the surrounding liquid. However, an examination of different nozzle geometries has shown that this can be overcome using non-circular nozzle exit geometries. One example is shown in FIGS. 3A, 3B and 3C. It uses a flattened nozzle exit which allows larger exit areas to be accommodated while still having adequately small radius of curvature, in one plane, so that the capillary forces will continue to restrain the gas in the nozzle after the ring advances upwards. Yet another means of achieving this for even larger diameter nozzles is by the use of fine restraining wires, or a fine mesh, across the nozzle face as in FIGS. 4A and 4B. These deform the interface surface between the gas in the nozzle and the surrounding liquid to create areas of small radius of surface curvature with their higher capillary forces. This allows the column of gas to remain pinned in the nozzle without an additional valve at the nozzle exit. Testing with these different kinds of nozzles has demonstrated that clean circular rings may be consistently generated despite the fact that the nozzles are not circular and may even have occlusions. Anyone skilled in understanding these phenomena will be able to conceive of other nozzle shapes that exploit these surface tension forces, aside from the methods in FIG. 3A, or FIG. 4B. But the innovative feature of this invention is that it makes ring bubbles possible because it uses natural surface tension forces to retain a static column of gas within the nozzle when the valve is closed and does so without requiring an additional valve.

These observations also suggests that the co-annular nozzles (such as described by Fohl, U.S. Pat. No. 3,589,603) are not appropriate for the generation of ring bubbles. In fact it is apparent that the center core of an annular nozzle will generate vorticity of the wrong sign in the central part of the outward flowing stream and this can interfere with the mechanism that has been described.

Another important feature of the concept is that a sustained flow through the nozzle will exist so long as the valve is open since the accumulator, 4, has a volume that is substantially larger than the volume of the ring 11. In other words the pressure in the accumulator does not markedly fall while the valve is open.

Advantages Over Prior Art

The invention that has been described recognizes that the generation of gas-filled vortex rings depends on the impulsive ejection of a small quantity of gas into a host liquid. The gas need not be limited to air, and the liquid need not be limited to water. This invention offers a number of features over the prior art which was described previously.

Consider, for example, the present invention in relation to the three embodiments of Takahashi et al., whose characteristics have already been discussed:

1. The third embodiment of Takahashi et al., does make use of a timed electrically operated valve, but it controls the flow of gas into an accumulator. An important difference is that the present invention uses an electrically actuated valve, 6, to control the flow not into, but out of the accumulator, 5. By this important difference, the duration of the flow exiting the nozzle, 8, is directly determined by the duration of the open time of the valve. That is not the case with the third embodiment of Takahashi et al., which requires significant mechanical reconstruction to change the duration of the nozzle flow since that is determined by the accumulator volume, the source pressure and resiliency of the second elastic valve.

2. Likewise, in the first and second embodiments of Takahashi et al., no easy means exists for changing the duration of the pulsed flow. That may be done easily with the present device since the timing circuit, 7, that operates the solenoid valve, may have its output pulse width changed by simply adjusting a potentiometer in the circuit.

3. Significant mechanical reconfiguration of the devices described by Takahashi et al. (such as changes to the valve springs etc.) is needed to change the pressure at which the devices operate, and hence the characteristics of the developing ring vortex. The operating pressure of the present invention can be easily changed by simply adjusting the regulator, 2.

4. All three embodiments of Takahashi et al., require a second elastic valve at the exit of the in order to operate. The present invention eliminates that need. Instead, surface tension forces are exploited in a novel way to contain the gas in the nozzle when the flow has stopped. This does not require any moving parts and is a considerably simpler approach since it will never wear out or leak.

5. In all three embodiments of Takahashi et al., the pressure in the accumulator is not constant but must decay during operation if the devices are to work and the second elastic valve is to close. An individual with expertise in the art will recognize that this kind of decaying flow is not ideal for the production of ring vortices. Sustained pressure during the duration of the flow is preferred. For the present invention, the accumulator may be made as large as desired in relation to the volume of gas expelled thereby maintaining a near-constant source pressure. The embodiments of Takahashi et al., do not allow this.

6. The present invention allows a ring to be performed at the precise moment that the valve, 6, is opened by the timing circuit, 7. This allows controlled sequences of rings to be generated in any desired frequency. In addition, if computer control is used to produce a sequence of timing pulses of different duration to open and close the valve, 6, then the present device can produce arrays of different size rings in any predetermined order. That is not the case with the devices of Takahashi et al., which will only produce one kind of ring when an adequately high pressure is finally reached in the accumulator.

The preceding considerations document the significant differences between the present invention and that of Takahashi et al., as well as the benefits that accrue to the present invention because of those differences. In simplest terms, the present invention exploits surface tension to eliminate the need for any second valve at the nozzle exit. Also, it uses an electrically operated valve to control the flow from an accumulator, as opposed to feeding a flow into an accumulator whose outflow is controlled by that second valve.

To someone with expertise in the art, the present invention is therefore not captured in the invention of Takahashi et al. The present invention is a new concept, exploiting vorticity generation in a nozzle and surface tension forces, and which have been found through experimentation by the present inventor, to provide the very specialized and ideal conditions needed for the formation of gas-filled ring vortices. Because these operational principles are not mentioned by Takahashi et al. and are significantly different from the principles they describe, an examination of their devices of does not lead someone skilled in the art to derive the present invention or to understand how the present invention works. The present invention and its successful operation are not obvious consequences of their descriptions.

Consider now the advantages of the present invention in relation to the two embodiments of the invention of Cullen that were described previously:

1. The present invention shows that annular nozzles as suggested by Cullen are not the best for ring generation, and that the nozzles need not even be circular. This is a new finding that the present invention exploits.

2. The present invention is a device that eliminates, through the novel use of surface tension forces, the need for any small valve at the end of the discharge tube used in the first embodiment of Cullen.

3. The second embodiment of Cullen is very like the third embodiment of Takahashi et al., and uses an electrically operated valve to pressurize a feedline and accumulator which terminates with a second valve, or array of valves.

As stated previously, the present invention differs significantly from this kind of embodiment through elimination of the second valve, and the fact that in the present device, the electric valve feeds pressurized gas directly from an accumulator to the nozzle exit. The consequences and significant advantages of these differences have already been described (see paragraph number [0040], subparagraph 1).

To someone skilled in the art, it will be apparent that the present invention is not an obvious outcome of the embodiments described by Cullen and uses principles of operation that are entirely different. It represents a new method for the production of gas-filled vortex rings.

Finally, consider the advantages of the present invention in relation to the two embodiments of Whiteis:

1. The first embodiment of Whiteis uses a tilting platform to direct a confined bubble of buoyant gas into a nozzle. To one skilled in the art, this approach will clearly be recognized as being significantly different from the present invention. However, a tilting platform, being mechanical, can not be expected to operate or at very rapid rates and the buoyancy limits the device to low pressures. The advantage of the present invention over that device is that it can operate at high pressures and at high repetition rates and with very short duration pulses.

2. The second embodiment of Whiteis uses an inverted dome to confine pressure that is manually released by an operator. It requires the operator to have the considerable skill necessary to be able to repeatedly release the gas at just the right volume and at just the correct rate to make gas-filled rings. The present invention will operate continuously and once correctly set, will consistently deliver the correct amount of gas over the correct duration of time to generate identical rings repeatedly.

The present invention can therefore be seen to be a substantially different concept over the devices of Whiteis and offers certain advantages to the controlled production of vortex ring bubbles. It is a new approach exploiting different physical principles and is not an obvious derivation from that device.

In summary, and from the foregoing, it may be recognized that the present invention offers the following features over the prior art:

1. It allows vortex ring bubbles to be formed without requiring multiple valves.

2. It further recognizes that the pressure of the source of gas and the duration of the pulse are the two main parameters which will determine whether or not a vortex ring will form for a given size exit nozzle.

3. This invention allows the pressure of the supply gas to be directly and repeatedly controlled. For a given timing pulse duration, low pressure will give rise to rings with lower core circulation than will high pressures. These rings move upwards more slowly and therefore have time to spread to larger overall diameters.

4. This invention allows the duration of the flow of the gas, referred to as the pulse of gas, to be directly and repeatedly controlled. For a given accumulator pressure, short pulses will give rise to thin rings, while longer pulse duration will give rise to thicker rings.

Figure 5:
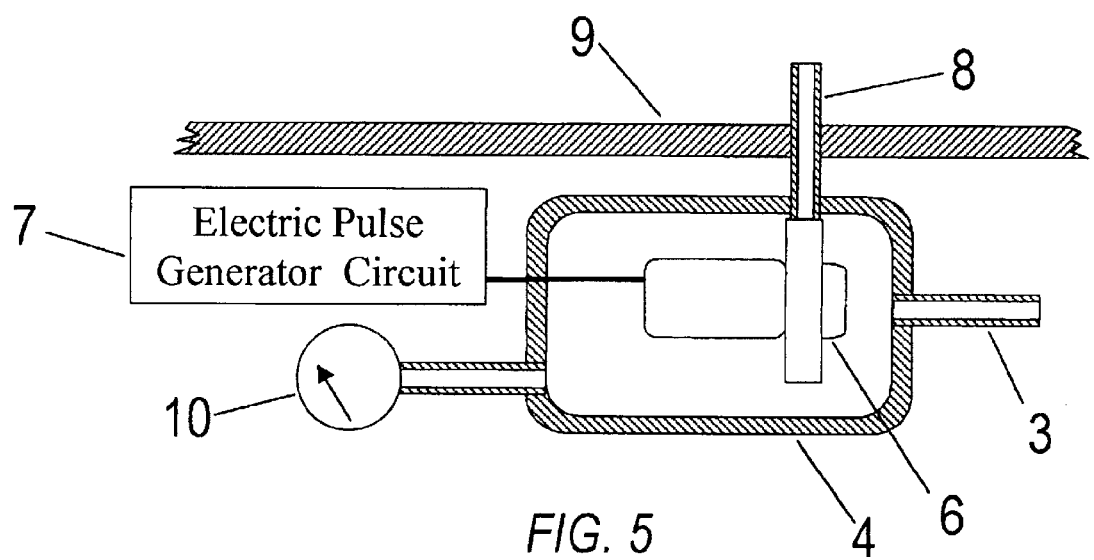
FIG. 5 depicts an alternative embodiment of the invention shown in FIG. 1.

5. Because of these control features offered by the invention, then the size and thickness of the gas-filled vortex rings can be directly controlled in a single apparatus. Variation of either of these parameters, within limits, allows rings of different geometries to be generated, also within limits, with a single apparatus. The geometry of the apparatus need not be changed to change these parameters. The operator can "dial in" the desired conditions for a given nozzle diameter.
6. Also because of these control features, the precise time at which the ring is formed can be specified. This allows controlled sequences of the rings to be generated in any desired frequency, or even in a predetermined order.
7. This invention further allows for the creation of small rings which generally require higher pressures and shorter pulses. The inventions of the prior art do not adapt well, or do not adapt at all to these kinds of conditions.
8. The invention shows that the geometry of the exit nozzle need not be circular and that a variety of shapes will work, with the greatest advantage being offered by those shapes that exploit surface tension forces to pin the column of gas in the discharge tube after the flow has been shut off Alternative Embodiments .An alternative embodiment of the invention is shown in FIG. 5 in which the solenoid valve 6 is placed inside the accumulator 4, thereby eliminating the connection tube 5 shown previously in FIG. 1. This leads to a device that operates in precisely the same fashion, but which has a smaller and more compact volume.

Figure 6:
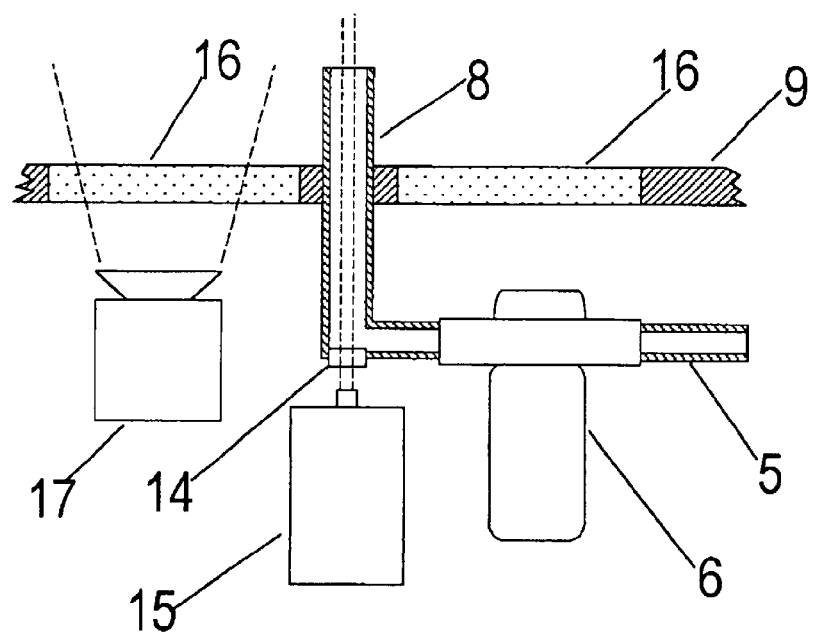
FIG. 6 depicts two methods by which the rings generated with this invention may be illuminated.

Yet another variation of the invention is shown in FIG. 6 which depicts the way illumination can be built into the invention so that it can be used in a decorative application. In this embodiment, the nozzle discharge tube 8 has a right-angle bend into which a small transparent window or lens 14 has been installed. A light source 15 such as a small light bulb, a light emitting diode or a small solid state laser is positioned to shine light up through this window and illuminate the host liquid into which the vortex rings are injected. The light illuminates these rings as they travel upwards through the host liquid creating a pleasing and unusual visual effect. Alternatively, the floor of the containment vessel 9 can be made of some transparent material or fitted with a window 16 and a light source 17 placed below it to also illuminate the rings as they travel upwards.

Figure 7:
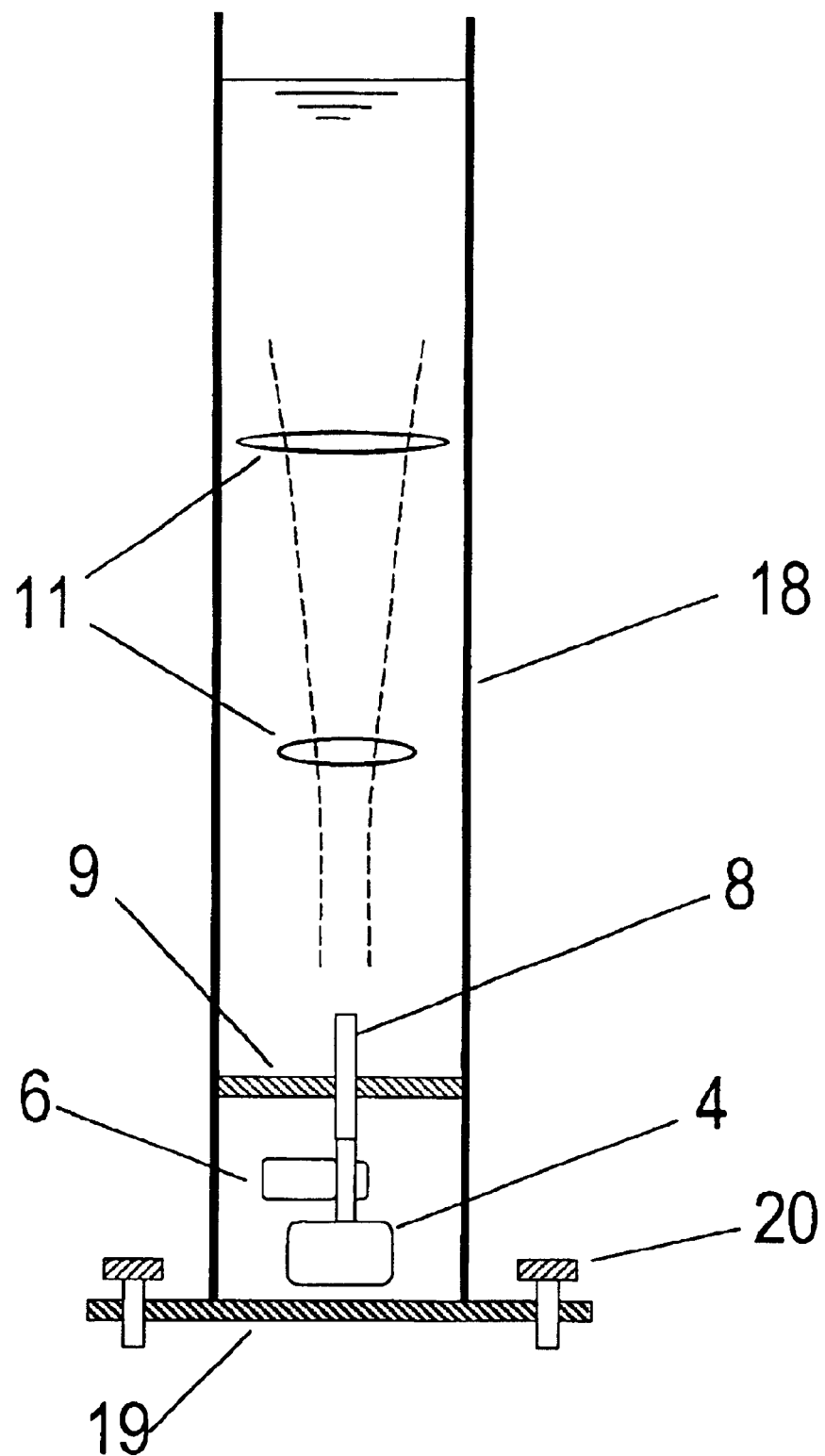
FIG. 7 depicts one possible application of the invention for producing rising vortex rings in a vertical tube and which may be used for decorative purposes.

A possible apparatus for the decorative display of these rings is depicted in FIG. 7, in which the components of either FIG. 1 or FIG. 5 or FIG. 6 or like embodiment are installed into a transparent tube 18. This tube is mounted on a base 19 with three or more adjusting screw supports 20 so that the tube may easily be positioned in the vertical. The transparent tube 18 can be of any desired diameter and length and cross section, although circular is to be preferred. The tube is filled with the host liquid, most likely water. Also, but not shown are the electronic circuitry, the light source, and the source of pressurized air which may also be installed in the lower part of the tube with the other components. The source of pressurized air for this device can be any source of compressed air, such as a commonly available aquarium pump or any other electric pump. The timing of the circuits can be set to create sequences of vortex rings that travel slowly up the column of water in a repetitive and pleasing fashion. By adjusting the time between the pulses vortex rings can be created which overtake each other and pass though one another. A device such as this may take the form of a free standing decoration, or it may be incorporated into the legs of an unusual table or incorporated into some other piece of furniture, such as a rack for holding compact disks, in a similarly decorative way.

Figure 8:
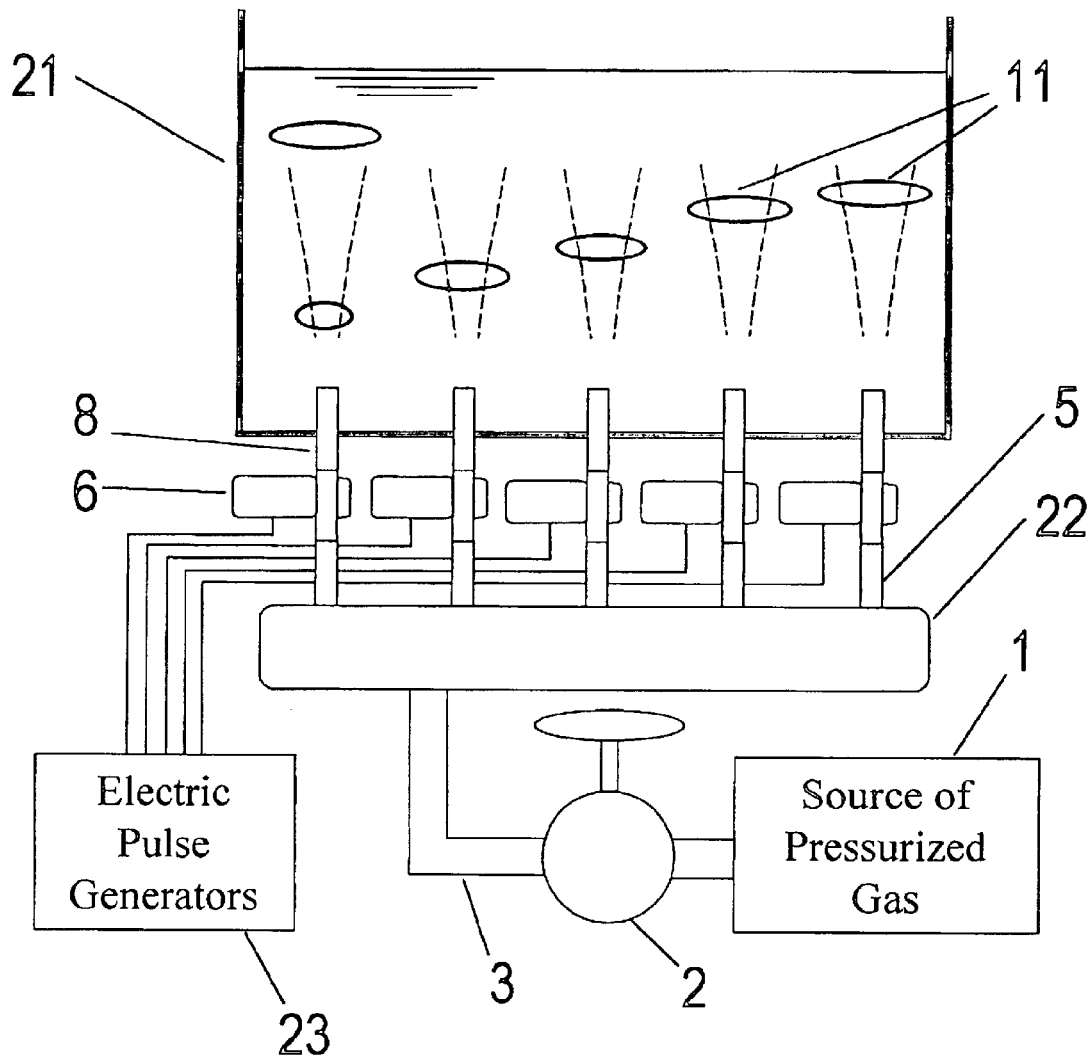
FIG. 8 depicts an alternative application of the invention in which a plurality of the devices is used to create unusual and visually captivating arrays of ring bubbles.

Another embodiment of the invention is depicted in FIG. 8 in which an array or plurality of the devices is distributed across the lower surface of a tank or vessel 21 in some kind of predetermined array. The tank may have transparent walls to allow easy viewing of the liquid inside. Each of these devices has its own valve 6 and nozzle 8, but may be connected to a common accumulator 22. The electrical timing pulses are derived from a multiple pulse generator system 23 that issues multiple timing pulses in any operator-defined controlled pattern and sequence. Because the invention offers a means of controlling the precise time at which rings are generated, this embodiment allows some spectacular and pleasing arrays of vortex rings to be repetitively established. As the rings travel upwards they will undergo complex interactions of vortex entanglement as they evolve. Depending on the geometry and timings for the valves, the resulting display is very dynamic and engaging. It would be very suitable for commercial advertising as it quickly captures the attention of the viewer due to its unusual and unexpected behavior.

Other uses for this invention can be as follows, but are not limited to the following:
1. Single devices or multiple arrays of devices can be used as a decorative feature in swimming pools, decorative pools, ponds, jacuzzis or fountains
2. Single devices or multiple arrays of devices can be used as the basis for toys for children to use in pools or bathtubs.
3. Single devices or multiple arrays of devices can be used for special effects in the cinema, film making or commercial television
4. Single devices or multiple arrays of devices can be used as a device for advertising either in commercial film and video
5. The device, or arrays of devices, can be used in commercial establishments to advertise products such as beverages
6. If the gas used is a combustible mixture, then with an additional ignition source, unusual underwater circular explosions and flames can be produced which have value as special effect features for cinematography
7. The flow field of the vortex ring is repeatable and can be used to calibrate scientific instruments that are used to measure fluid flows such as laser velocimeters, particle imaging velocimeters and hot-wire anemometers
8. Because the vortex rings are highly repeatable, with a repeatable surrounding flow field, then when generated in arrays from multiple sources, they give rise unusual vortex interactions which are an object of scientific study in their own right
9. The invention may be used as a demonstration device to instruct and educate students in the behavior of ring vortices and surface tension phenomena

What I claim as my invention is:
1. An apparatus for providing a simple and direct means of creating vortex ring bubbles of gas in a liquid medium, comprising:
  a source of high pressure gas connected to an inlet of a regulator valve;
  an accumulator volume having a gas inlet and a gas outlet, said gas inlet of the accumulator volume being connected to the outlet of said regulator valve;
  a gas conduit extending from said accumulator volume gas outlet to a nozzle outlet;
  an electrically operated solenoid valve arranged along said gas conduit to control the flow of gas out of the accumulator volume;
  an electrical circuit operable to open and close said solenoid valve for a predetermined period; and
  wherein said nozzle outlet may be circular, or may have a flattened outlet, or said outlet may be covered with a fine wire mesh, through which the flow of gas from the solenoid valve passes and which is installed protruding through a floor of a tank of liquid.

2. A method of producing controlled vortex ring bubbles of gas in a liquid, at a precisely defined time, using the apparatus of claim 1, the method comprising the steps of:

pressurizing the accumulator volume with gas to a desired pressure;

generating an electrical pulse of desired duration to momentarily open the solenoid valve and connect the gas in the accumulator volume to the nozzle outlet;

exhausting the pressurized gas from the accumulator volume, through the nozzle outlet and forming a bubble at the outlet of the nozzle that self organizes into a gas-filled vortex ring;

closing the solenoid valve, wherein the ring vortex separates from the nozzle outlet and travels upwards under buoyancy forces and self induced motion, the gas remaining in the nozzle being captured within the nozzle by surface tension forces at the plane of the nozzle outlet.

3. The method of claim 2, further comprising operating the solenoid valve with a sequence of repetitive pulses to generate repetitive arrays or sequences of rings at any desired rate.

4. The method of claim 2, further comprising:

independently controlling the pressure of the gas within the accumulator volume, and independently controlling the duration of the pulse so that the size and thickness of the vortex ring bubbles of gas are controllable in a single apparatus.

* * * * *